United States Patent
Wei et al.

[11] Patent Number: 5,851,805
[45] Date of Patent: Dec. 22, 1998

[54] METHOD FOR PRODUCING DNA FROM MRNA

[75] Inventors: Dong Wei; Veronica M. Maher, both of East Lansing; Joseph Justin McCormick, Morrice, all of Mich.

[73] Assignee: Board of Trustees operating Michigan State University, East Lansing, Mich.

[21] Appl. No.: 784,751

[22] Filed: Jan. 16, 1997

[51] Int. Cl.$^6$ .......................... C07H 19/00; C07H 21/04; C07H 21/00; C12P 19/34

[52] U.S. Cl. ..................... 435/91.2; 536/22.1; 536/24.2; 536/24.53; 536/25.34; 536/25.4; 435/91.52; 435/395; 435/810; 435/7.1; 435/91.51; 424/85.8

[58] Field of Search ................................. 536/22.1, 24.2, 536/24.33, 25.32, 25.4; 435/91.2, 810, 91.52, 395, 7.1, 91.51; 424/85.8

[56] References Cited

U.S. PATENT DOCUMENTS

| | | |
|---|---|---|
| 4,683,202 | 7/1987 | Mullis . |
| 5,066,584 | 11/1991 | Gyllensten et al. . |
| 5,093,245 | 3/1992 | Keith et al. ............................... 435/91 |
| 5,106,727 | 4/1992 | Hartley et al. . |
| 5,132,215 | 7/1992 | Jayaraman et al. . |
| 5,169,766 | 12/1992 | Schuster et al. . |
| 5,262,311 | 11/1993 | Pardee et al. . |
| 5,348,853 | 9/1994 | Wang et al. . |
| 5,413,924 | 5/1995 | Kosak et al. ............................ 435/177 |

OTHER PUBLICATIONS

Strathdee et al Nature 356:763–767 (1992).
Legerski, R. and C. Peterson, Nature, 359:70–73 (1992).
Zimmerman, C.R., et al., Cell 21:709–715 (1980).
Liang, P. and A.B. Pardee, Science 257:967–971 (1992).
Aiello, L.P. et al., Proc. Natl. Acad. Sci. USA 91:6231–6235 (1994).
Utans, U., et al., Proc. Natl. Acad. Sci. USA 91:6463–6467 (1994).
Sambrook, J. et al., in Molecular Cloning: A Laboratory Manual (Cold Spring Harbor Lab., Cold Spring Harbor, NY, 8.3–8.32 (1989).

*Primary Examiner*—W. Gary Jones
*Assistant Examiner*—Joyce Tung
*Attorney, Agent, or Firm*—Ian C. McLeod

[57] ABSTRACT

An improved method for amplifying cDNA fragments corresponding to the mRNA species expressed in cells is described. The method involves priming the mRNA with a first labeled synthetic oligodeoxynucleotide and then reverse transcribing the mRNA to produce a mRNA:cDNA hybrid; and then producing a double-stranded DNA from the hybrid. This DNA is digested with a restriction endonuclease and then a synthetic DNA linker, carrying a second label, is ligated at the cut to the DNA strand containing the 5' phosphate group. The DNA is then isolated with a first reagent which binds the second label. The DNA fragments of interest are then isolated using a second reagent which binds the first label. The isolated DNA fragments are amplified using polymerase chain reaction, and then separated on a sequencing gel. The method is particularly useful for comparing the mRNA species expressed in the cells of various samples.

27 Claims, 4 Drawing Sheets

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 25
        ( B ) TYPE: Nucleic Acid
        ( C ) STRANDEDNESS: Single
        ( D ) TOPOLOGY: Linear ( i i ) MOLECULE TYPE: DNA ( i i i ) HYPOTHETICAL: No ( i v ) ANTI-SENSE: No ( v ) FRAGMENT TYPE:

( v i ) ORIGINAL SOURCE:
        ( A ) ORGANISM: N/A
        ( B ) STRAIN: N/A
        ( C ) INDIVIDUAL ISOLATE: N/A
        ( D ) DEVELOPMENTAL STAGE: N/A
        ( E ) HAPLOTYPE: N/A
        ( F ) TISSUE TYPE: N/A
        ( G ) CELL TYPE: N/A
        ( H ) CELL LINE: N/A
        ( I ) ORGANELLE: N/A ( v i i ) IMMEDIATE SOURCE: N/A ( v i i i ) POSITION IN GENOME: N/A ( i x ) FEATURE:
        ( A ) NAME/KEY:
        ( B ) LOCATION:
        ( C ) IDENTIFICATION METHOD: sequencing
        ( D ) OTHER INFORMATION: Synthetic ( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( K ) RELEVANT RESIDUES IN SEQ ID NO:

( x i ) SEQUENCE DESCRIPTION: SEQ ID NO:1:

GTCTTATGTA TGTATCTCGA ATGCT 25

( 2 ) INFORMATION FOR SEQ ID NO:2:

( i ) SEQUENCE CHARACTERISTICS:
        ( A ) LENGTH: 12
        ( B ) TYPE: Nucleic Acid
        ( C ) STRANDEDNESS: Single
        ( D ) TOPOLOGY: Linear ( i i ) MOLECULE TYPE: DNA ( i i i ) HYPOTHETICAL: No ( i v ) ANTI-SENSE: No ( v ) FRAGMENT TYPE:

( v i ) ORIGINAL SOURCE:
        ( A ) ORGANISM: N/A
        ( B ) STRAIN: N/A
        ( C ) INDIVIDUAL ISOLATE: N/A

```
        (D) DEVELOPMENTAL STAGE: N/A
        (E) HAPLOTYPE: N/A
        (F) TISSUE TYPE: N/A
        (G) CELL TYPE: N/A
        (H) CELL LINE: N/A
        (I) ORGANELLE: N/A (vii) IMMEDIATE SOURCE: N/A (viii) POSITION IN GENOME: N/A (ix) FEATURE:
        (A) NAME/KEY:
        (B) LOCATION:
        (C) IDENTIFICATION METHOD: sequencing
        (D) OTHER INFORMATION: Synthetic nucleotide (x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (K) RELEVANT RESIDUES IN SEQ ID NO:

(xi) SEQUENCE DESCRIPTION: SEQ ID NO:2:

AGCATTCGAG AT                                                                    12
```

METHOD FOR PRODUCING DNA FROM MRNA

BACKGROUND OF THE INVENTION

(1) Summary of the Invention

The present invention relates to a method for producing DNA from messenger RNA (mRNA). In particular, the present invention relates to a method for isolating and cloning mRNA species, referred to as Restriction Enzyme RNA Fingerprinting (RERF). The method is also useful for producing DNA or RNA probes.

(2) Background of the Invention

Cells of higher organisms, such as humans, contain about 100,000 different genes. However, in an individual cell, only about 15,000 genes are expressed and these are expressed at different frequencies. Differential expression of genes is believed to be the basis of basic life processes, such as differentiation, aging, cell cycle regulation, and tumorigenesis. If one were readily able to identify the gene or genes that are specifically expressed or not expressed in cells or expressed at different levels in cells with a certain phenotype, such as tumorigenic cells compared to the parental cells, this would provide a valuable means of determining the molecular and biological mechanisms responsible for the characteristic of interest.

In cases where information can be obtained concerning at least part of the sequence of a gene of interest or of the protein it encodes, several direct cloning methods can be used to identify the gene. However, even when such information is lacking, one can identify a gene by using complementary DNA (cDNA) library expression cloning (for example, See Strathdee et al., Nature 356:763–767 (1992) and Legerski, R. and C. Peterson, Nature, 359:70–73 (1992)) or by using subtractive hybridization of mRNA (Zimmerman, C. R., et al., Cell 21:709–715 (1980)) or mRNA differential display (Liang, P. and A. B. Pardee, Science 257:967–971 (1992); Aiello, L. P. et al., Proc. Natl. Acad. Sci. USA 91:6231–6235 (1994); Utans, U., et al., Proc. Natl. Acad. Sci. USA 91:6463–6467 (1994)).

For cDNA expression cloning or for subtractive hybridization, a comprehensive cDNA library prepared from cells of a specific type is required. Construction of a cDNA library begins by extracting mRNA from the desired cells (Sambrook, J. et al., in Molecular Cloning: A Laboratory Manual. (Cold Spring Harbor Lab., Cold Spring Harbor, N.Y., 8.3–8.32 (1989)). Since mRNA from eukaryotic cells contains a poly A tail at the 3' end, an oligodeoxynucleotide primer of 12–18 thymidine residues, i.e., oligo (dT) primer, can be annealed to the 3' end of the mRNA, and the first strand of cDNA can be synthesized using reverse transcriptase. Several methods can be used to synthesize the second strand of the cDNA, but replacement synthesis is the most efficient (Sambrook, J., et al., in Molecular Cloning: A Laboratory Manual. (Cold Spring Harbor Lab., Cold Spring Harbor, N.Y.), 8.3–8.32 (1989)).

In replacement synthesis, a ribonuclease, such as ribonuclease H (RNase H), is used to generate nicks, i.e., cleave the phosphodiester backbone in the mRNA strand of the mRNA:cDNA hybrid. A DNA polymerase such as *Escherichia coli* DNA polymerase I or Klenow fragment is then used to extend the 3'-hydroxyl at the nicks to synthesize the second strand of the cDNA and in doing so to displace the mRNA strand. This is a very efficient method to produce near full-length double-stranded cDNAs.

Once the double-stranded cDNA has been synthesized, the cDNA library is constructed by cloning the cDNAs into a plasmid or viral vector at a site downstream of a strong promoter to allow the efficient transcription of the cDNA. Such vectors usually carry two replication origins, one for replicating in bacteria and the other for replicating in the target eukaryotic cells.

If cells exhibiting a specific phenotype can be selected for or screened for in some way, cDNA expression cloning can be used to identify the gene responsible for this specific characteristic. A cDNA library can be constructed using mRNAs from cells that have a specific phenotype of interest, and transfected into the target cells that lack this phenotype. The transfectants can then be selected or screened to find those that have acquired the specific phenotype. These cells should now contain the gene that is responsible for the desired trait. The plasmid or viral vector containing that gene can then be rescued from progeny cells of the transfectant, and the gene can be sequenced. This method is straightforward. However, it requires a very efficient selection system and can only be used in cases in which the phenotype results from the expression of a single gene, since the chance of two (or more) specific genes being transfected into the same target cell is very small.

In cases where a particular phenotype cannot be selected for or screened for, subtractive hybridization can be used to enrich for the mRNA of the gene of interest and ultimately to identify the gene responsible for the phenotype of interest. Basically, with this method mRNA is extracted from the cells that express the desired phenotype, and radiolabeled first strand cDNA is synthesized with reverse transcriptase as described above and hybridized in solution to a large excess of mRNA from a closely related cell that lacks the phenotype. After hybridization, the cDNA:mRNA hybrids, which represent the set of mRNAs that are expressed by both cell populations, are removed from the solution. The radiolabeled cDNA that cannot form cDNA:mRNA hybrids, and thus remains in solution, should correspond to the mRNAs that are uniquely expressed in the cell population with the desired phenotype. In this way, the solution is highly enriched for cDNA from the desired gene, and the radiolabeled cDNA can then be used to screen a cDNA library or genomic DNA library. The clones that are identified by this hybridization screening process can then be verified as containing the desired gene by Northern blotting using cells that lack or possess the desired phenotype. Although conceptionally straightforward, this subtractive hybridization method is very laborious. Furthermore, if the level of expression of the gene in the desired population is only several times higher than that in the population lacking the phenotype, it is difficult to clone the desired gene using this method.

In 1992, Liang and Pardee published a method to visualize essentially all the mRNAs being synthesized in a mammalian cell (Liang, P. and A. B. Pardee, Science 257:967–971 (1992); U.S. Pat. No. 5,262,311). They named their method "Differential Display Reverse Transcription-Polymerase Chain Reaction" (DDRT-PCR). In this method, mRNAs from a population of cells with a particular phenotype and a control cell population lacking the phenotype are reverse transcribed with 3' oligodeoxynucleotide that consists of 11 deoxythymine residues, anchored at the 5' end of the polyadenylate (poly(A)) tail by the presence at the 3' end of the oligodeoxynucleotide of an M and N, where M is deoxyguanylate (dG), deoxycytidylate (dC) or deoxyadenylate (dA) and N is dG, dC, dA or deoxythmidylate (dT) i.e., oligo(dT)MN primer. The corresponding cDNAs are then amplified by PCR using the oligo(dT)MN primer in conjunction with a series of second oligodeoxynucleotide primers of arbitrary sequence that will anneal randomly to the various cDNA molecules. Then the amplified cDNA subpopulations representing 3'-termini of mRNAs of various lengths, as defined by every pair of primers, are analyzed on a DNA sequencing gel. These investigators estimated that by varying the primer combinations, statistically all mRNA sequences upstream of the oligo(dT)MN primer can be displayed. To verify that a difference in the abundance of cDNA corresponding to the 3'-terminus of a specific mRNA sequence on a gel actually represents a change in the level of expression of that mRNA in the cells of interest, one then uses the cDNA fragment generated by the procedure to analyze expression of the corresponding cellular gene by Northern blotting. In less than 50% of the cases reported by Liang and Pardee (1992), Northern blotting confirmed the differences observed by the Differential Display method. In the case of subsequent reports in the literature using this technique and in the case of unpublished data obtained in the inventors' laboratory, the percentage of confirmation can be as low as 10%.

Although the method of Liang and Pardee (1992) offers many technical advantages over previous methods, such as subtractive hybridization, in identifying and cloning differentially-expressed genes (e.g., simplicity, sensitivity, and speed), it has certain limitations. The length of the second oligodeoxynucleotide of arbitrary sequence (random primer) to be used represents a necessary compromise. In order to recognize as many mRNA species as possible, Liang and Pardee (1992) calculated that the second primer of arbitrary sequence needed to be a 6-mer or 7-mer. However, in order to amplify a specific sequence with a high degree of specificity using the PCR procedure, the arbitrary sequence primer needed to be as long as possible. A third consideration was that the oligo(dT)MN primer needed to be a length similar to that of the arbitrary sequence primer so that both primers would have a similar melting temperature. Empirically, Liang and Pardee (1992) found that an arbitrary sequence 9-mer and an anchored $dT_{12}MN$ primer failed to produce specific bands, but that a 10-mer for the arbitrary sequence primer and an anchored $dT_{12}MN$ did so. Use of such relatively short primers dictates use of 40° C. as the annealing temperature during PCR, which compromises the specificity. An additional difficulty with the DDRT-PCR method is that, at times, it produces a high background. In addition, the presence of a single band is not indicative of a single cDNA fragment. It can sometimes consist of a mixture of several different cDNA fragments of the same length. In such cases, subcloning procedures must be employed to separate the fragments, and Northern blotting analysis with each one is required to identify those that are differentially expressed. The necessary reliance on relatively short primers, which results in 50% to 90% of the differences noted not being confirmed by Northern blotting using the cDNA, limits the usefulness of the technique.

In the patent arts U.S. Pat. Nos. 4,683,202 to Mullis; 5,106,727 to Hartley et al; 5,132,215 to Javaraman et al; 5,066,584 to Gyllensten et al; 5,169,766 to Schuster et al and 5,348,853 to Wang et al describe various RNA and DNA duplication and amplification techniques. There are numerous related patents. The definitions in these references are used in the present application, particularly those in Hartley et al.

OBJECTS

It is therefore an object of the present invention to provide a method and kit for producing DNA from mRNA. In particular, it is an object of the present invention to provide a method and kit which is very reliable in detecting differences in mRNA between related cell populations. The present invention also relates to a method for producing DNA from mRNA which can be used for probes for mRNA or DNA. These and other objects will become increasingly apparent by reference to the following description and the drawings.

DESCRIPTION OF PREFERRED EMBODIMENTS

The present invention relates to a method for producing DNA from mRNA in a sample which comprises:

(a) isolating RNA from the sample;

(b) priming the mRNA with a synthetic oligodeoxynucleotide that can hybridize with the polyadenylate (polyA) tail of mRNA and one non-adenylate nucleotide, and consists of polydeoxythymidylate (dT), which has a first label at its 5' end and is anchored at its 3' end by a deoxynucleotide (M), wherein M is selected from the group consisting of dG, dC and dA;

(c) reverse transcribing the mRNA to produce a mRNA:cDNA hybrid;

(d) producing a double-stranded DNA from the mRNA:cDNA hybrid;

(e) digesting the double-stranded DNA with a restriction endonuclease to produce a cut in the double-stranded DNA;

(f) ligating the double-stranded DNA at the cut with one of a pair of synthetic oligodeoxynucleotides, one of which is longer than the other, forming linker DNA which has a staggered end and a blunt end, wherein one of the oligodeoxynucleotides has a second label, different from the first label, at its staggered end and is the oligodeoxynucleotide that is ligated at the blunt end to one strand of the double-stranded DNA;

(g) isolating the double-stranded DNA containing the second label with a first reagent which binds the second label;

(h) isolating the double-stranded DNA containing the first label with a second reagent which binds the first label, wherein the isolated DNA is now free of mRNA;

(i) amplifying the isolated DNA by a polymerase chain reaction (PCR); and (j) separating the amplified DNA.

The present invention also relates to a method for identifying mRNA produced by a cell population which comprises:

(a) isolating RNA from a population of cells;

(b) priming the mRNA with a synthetic oligodeoxynucleotide that can hybridize to the polyA tail of the mRNA and has the formula $(dT)_xM$ which has a first label at its 5' end, wherein dT is deoxythymidylate, M is selected from the group consisting of dG, dC and dA, and x is a whole number between 20 and 28;

(c) reverse transcribing the mRNA to produce a mRNA:cDNA hybrid;

(d) producing a double-stranded DNA from the mRNA:cDNA hybrid;

(e) digesting the double-stranded DNA with a restriction endonuclease to produce a cut in the double-stranded DNA;

(f) ligating the double-stranded DNA at the cut with one of a pair of synthetic oligodeoxynucleotides, one of which is longer than the other, forming linker DNA which has a staggered end and a blunt end, wherein one of the oligodeoxynucleotides has a second label, different from the first label, at its staggered end and is the oligodeoxynucleotide that is ligated at the blunt end to one strand of the double-stranded DNA;

(g) isolating the double-stranded DNA containing the second label with a first reagent which binds the second label;

(h) isolating the double-stranded DNA containing the first label with a second reagent which binds the first label, wherein the isolated DNA is now free of mRNA;

(i) amplifying the isolated DNA by a polymerase chain reaction (PCR); and (j) separating the amplified DNA, wherein the DNA identifies the mRNA produced by the population of cells.

The present invention also relates to a method for identifying mRNA produced by a set of cell populations which comprises:

(a) isolating RNA from one of the cell populations;

(b) priming the mRNA with a synthetic oligodeoxynucleotide that can hybridize to the polyA tail of the mRNA and has the formula $(dT)_xM$ which has a first label at its 5' end, wherein dT is deoxythymidylate, M is selected from the group consisting of dG, dC and dA and x is a whole number between 20 and 28;

(c) reverse transcribing the mRNA to produce a mRNA:cDNA hybrid;

(d) producing a double-stranded DNA from the mRNA:cDNA hybrid;

(e) digesting the double-stranded DNA with a restriction endonuclease to produce a cut in the double-stranded DNA;

(f) ligating the double-stranded DNA at the cut with one of a pair of synthetic oligodeoxynucleotides, one of which is longer than the other, forming linker DNA which has a staggered end and a blunt end, wherein one of the oligodeoxynucleotides has a second label, different from the first label, at its staggered end and is the oligodeoxynucleotide that is ligated at the blunt end to one strand of the double-stranded DNA;

(g) isolating the double-stranded DNA containing the second label with a first reagent which binds the second label;

(h) isolating the double-stranded DNA containing the first label with a second reagent which binds the first label, wherein the isolated DNA is now free of mRNA;

(i) amplifying the isolated DNA by a polymerase chain reaction (PCR); and (j) separating the amplified DNA, wherein the DNA identifies the mRNA produced by the cell population; and (k) repeating steps (a) to (j) with different endonucleases to detect differences in the mRNA in the set of cell populations.

The present invention also relates to a kit for producing DNA from the mRNA in a sample which comprises:

(A) a synthetic oligodeoxynucleotide which contain a first label and which is poly(dT)M, wherein M is selected from the group consisting of dG, dC, dA;

(B) a pair of synthetic oligodeoxynucleotides of unequal lengths, forming linker DNA, wherein the longer of the synthetic oligodeoxynucleotides has a label at its staggered end which is different from the first label;

(C) a first reagent which binds the second label;

(D) a second reagent which binds the first label, wherein the kit is used in a method which comprises:

(a) isolating RNA from the sample;

(b) priming the mRNA with the synthetic oligodeoxynucleotide which binds to the poly(A) tail of the mRNA and is anchored at its 5' end;

(c) reverse transcribing the mRNA to produce a mRNA:cDNA hybrid;

(d) producing a double-stranded DNA from the mRNA:cDNA hybrid;

(e) digesting the double-stranded DNA with a restriction endonuclease to produce a cut in the double-stranded DNA;

(f) ligating the double-stranded DNA at the cut with the longer of a pair of synthetic oligodeoxynucleotides that comprise the linker DNA at the blunt end of the linker;

(g) isolating the double-stranded DNA containing the second label with the first reagent which binds the second label; and (h) isolating the double-stranded DNA containing the first label with the second reagent which binds the first label, wherein the isolated DNA is now free of mRNA.

The present invention also relates to a kit for identifying mRNA in a cell population which comprises in separate containers:

(A) a synthetic oligomer which contains a first label of the formula $(dT)_xM$, wherein dT is polydeoxythymidylate, M is selected from the group consisting of dG, dC, dA and X is a whole number between 20 and 28;

(B) a pair of synthetic oligodeoxynucleotide primers, one of which is longer than the other, forming linker DNA which has a staggered end and a blunt end, wherein one of the oligodeoxynucleotides has a label at the staggered end which is different from the first label;

(C) a first reagent which binds to the second label; and (D) a second reagent which binds to the first label;

(E) multiple restriction endonucleases wherein the kit is used for identifying mRNA produced by a cell population which comprises:
  (a) isolating RNA from a cell population;
  (b) priming the mRNA with the synthetic oligodeoxynucleotide which binds to the poly(A) tail;
  (c) reverse transcribing the mRNA to produce a mRNA:cDNA hybrid;
  (d) producing a double-stranded DNA from the mRNA:cDNA hybrid;
  (e) digesting the double-stranded DNA with a restriction endonuclease to produce a cut in the double-stranded DNA;
  (f) ligating the double-stranded DNA at the cut with the longer of a pair of synthetic oligodeoxynucleotides comprising the linker DNA at the blunt end of the linker;
  (g) isolating the double-stranded DNA containing the second label with the first reagent which binds the second label;
  (h) isolating the double-stranded DNA containing the first label with the second reagent now binds the first label, wherein the isolated DNA is now free of mRNA;
  (i) amplifying the isolated DNA by a polymerase chain reaction (PCR);
  (j) separating the amplified DNA; and
  (k) repeating steps (a) to (j) for each of the restriction endonucleases and for different sets of cell populations in order to detect differences between the mRNA of the cell population.

The present invention provides a method for amplifying mRNA in a "sample". Such "samples" may include biological samples derived from a human or other animal source (such as, for example, blood, urine, saliva, biopsy samples, histology tissue samples, PAP smears, moles, warts, etc.) or from plant sources or samples derived from a bacterial preparation, as well as other samples (such as, for example, agricultural products, waste or drinking water, milk or other processed foodstuff, etc.). The template nucleic acid molecule is mRNA and may be either homologous to the source or heterologous to the source or both. For example, amplification of a human tissue sample infected with a virus may result in amplification of both viral and human sequences.

The term "endonucleases" means an enzyme which digests (cuts) DNA producing a staggered or blunt end cut. Examples of suitable blunt end endonucleases are BsaBI, BsrBI, EcoRV, ScaI, StuI, and XmnI.

"Reverse transcribing" refers to the process wherein a reverse transcriptase is used to produce a complementary DNA strand (cDNA) from mRNA, using a primer consisting of polydeoxythymidylate which binds mRNA.

The term "amplification" refers to an increase in the amount of a nucleic acid sequence wherein the sequences produced are the same as a starting sequence.

The phrase "DNA polymerase" means an enzyme which promotes the polymerization of nucleotides in a template-prescribed manner. The template in this instance dictates the sequence. DNA polymerases begin the synthesis of a new nucleic acid chain by adding nucleotides to the hydroxyl group at the 3'-end of a pre-existing RNA or DNA primer using a pre-existing DNA strand as the template. A preferred polymerase is the large proteolytic fragment of DNA polymerase I of the bacterium *E. coli,* commonly known as Klenow fragment. Other DNA polymerases, such as *E. coli* DNA polymerase I, and bacteriophage T7 DNA polymerase, may also be used to synthesize DNA.

It is necessary to provide to the assay mixture an amount of required cofactors such as $Mg^{++}$, and nucleoside triphosphates, i.e., DATP, dCTP, dGTP, dTTP, herein called "triphosphate substrates", in sufficient quantity to support the degree of DNA synthesis desired. The amount of deoxyribonucleotide triphosphate substrates required for substantial DNA synthesis using the Klenow polymerase typically will be in the range of about 50 $\mu$M to about 2 mM, preferably initially 400 $\mu$M concentration at the start of the synthesis. Nucleoside triphosphate analogues can be substituted or added to those specified above, provided that the base pairing, polymerase, and strand displacing functions are not adversely affected to the point that the amplification does not proceed to the desired extent.

The term "displaces" as used herein refers to the phenomenon in which a chemical, physical, or biological agent, for example, a DNA polymerase, causes the dissociation of a base-paired nucleic acid from its complementary strand in a 5'-to-3' direction in conjunction with, and in close proximity to, template-directed nucleic acid synthesis. Displacement begins at the 5'-end of a base-paired nucleic acid sequence and proceeds in consequence of nucleic acid synthesis immediately 5'-to the displacement site. Both the newly synthesized and displaced nucleic acids have the same base sequence which is complementary to the template nucleic acid strand. The strand displacement activity resides on the same molecule as DNA synthesis. DNA polymerases such as *E. coli* DNA polymerase I, the Klenow fragment of DNA polymerase I, the bacteriophage T7 DNA polymerase, and the bacteriophage T4 DNA polymerase, are enzymes which possess both polymerase activity and strand displacement activity. Agents such as helicases may be used in conjunction with polymerases which do not strand displace, in order to produce the effect of strand displacement, that is, displacement of a nucleic acid strand coupled to the synthesis of a nucleic acid strand of the same sequence.

As used herein, "priming" or "to prime" refers to the apposition of an oligodeoxynucleotide or nucleic acid to a template nucleic acid, whereby said apposition enables the polymerase to polymerize nucleotides into a nucleic acid which is complementary to the template nucleic acid.

The primer is preferably single stranded for maximum efficiency in amplification, but may alternatively be double-stranded. If double-stranded, the primer must first be treated, for example, by heating at a temperature sufficient to separate the strands, before being used to prepare extension products, preferably to about 90°–100° C. for about 1 to 10 minutes.

The oligodeoxynucleotide used as a primer for reverse transcription in the present invention is polydeoxythymidylate M, where M is selected from dG, dC and dA. The result is that the primer binds to the 3' end of the mRNA. The dT is preferably between 20 and 28 mer, although dT can be between 10 and 50.

The method of the present invention can be marketed in the form of kits. This requires that the ingredients for the method be packaged in separate containers.

The method of the present invention improves the specificity and versatility of displaying different species of mRNAs by using restriction enzyme digestion and ligation mediated polymerase chain reaction. Double-stranded cDNA is synthesized from mRNA and subjected to digestion with various restriction enzymes. The patterns of restriction enzyme cleavage are then determined using ligation mediated PCR. Since the genes expressed by each type of cell are unique, and the sequences recognized by restriction enzymes are constant, the pattern of cleavage by one type of restriction endonuclease of double-stranded DNA produced by replacement synthesis of cDNA from a particular type of cell is specific to each cell type, just like a fingerprint to a person. Therefore, this new method has been abbreviated by the acronym Restriction Enzyme RNA Fingerprinting (RERF).

Figure 1:
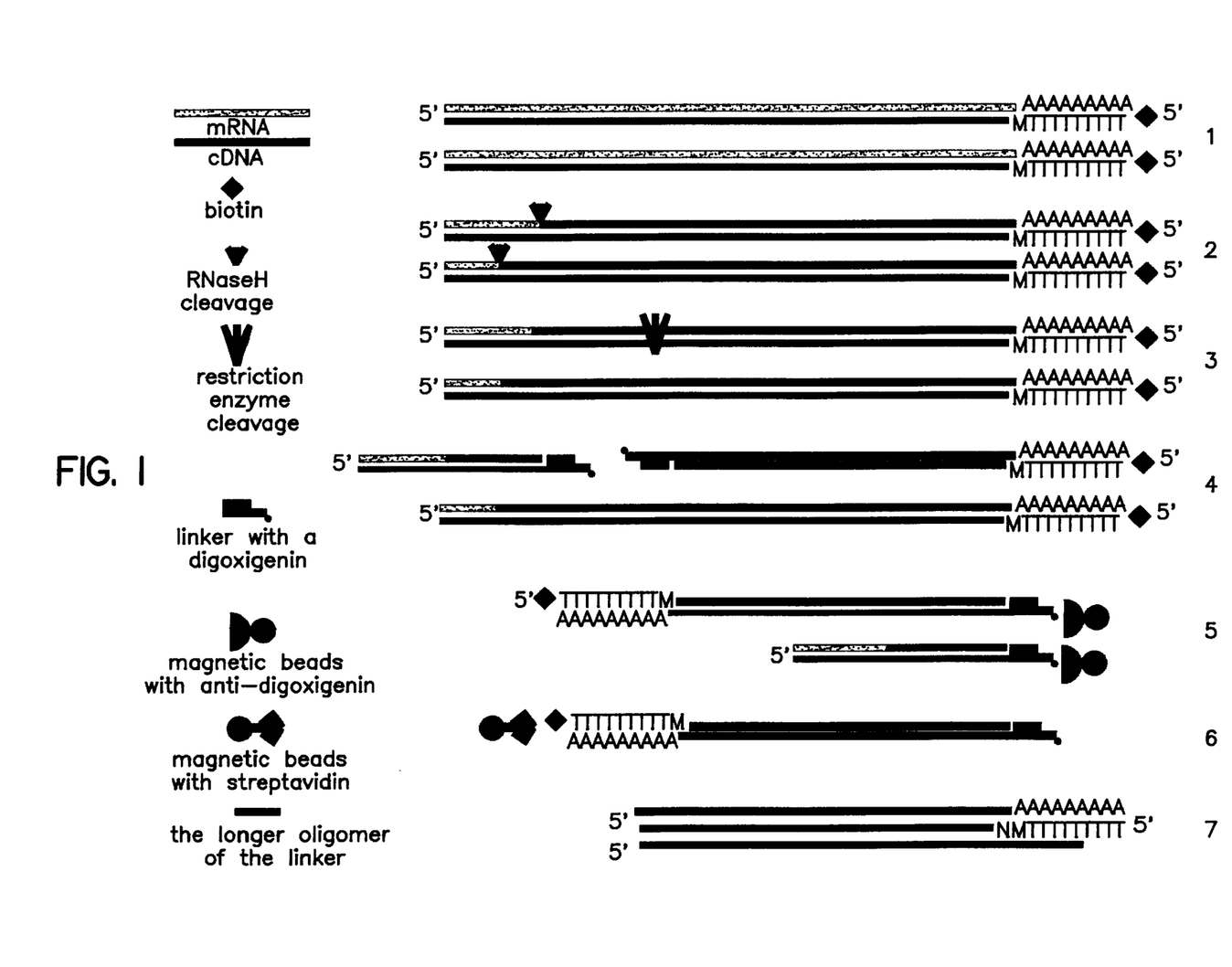
FIG. 1 is a schematic representation of the method according to the present invention.

The preferred seven steps (1–7) involved are shown schematically in FIG. 1:

1. A 5' biotinylated $dT_XM$ (M is an equal mixture of dG, dC and dA) is used to reverse transcribe the mRNAs to generate first strand complementary DNA (cDNA);

2. The mRNA:cDNA hybrids are subjected to limited RNase H digestion to produce random nicks in the mRNA, and the 3'-OH ends at nicks generated by RNase H are extended by the Klenow fragment of *Escherichia coli* DNA Polymerase I to produce a full-length complementary (second) DNA strand;

3. An appropriate restriction enzyme that recognizes a sequence of at least six nucleotides and produces a blunt end cut, e.g., StuI, is used to digest the DNA:DNA duplex;

4. An asymmetric linker is then ligated to the blunt end on each side of the cut using T4 DNA ligase. The linker is composed of a longer oligomer and a shorter oligomer that is complementary to the 3' end of the longer oligomer (see FIG. 1 Step 4). This assures that there is only one blunt end and that it is located at the 3' end of the longer oligomer. The 5' end of the longer oligomer contains a digoxigenin molecule. Since T4 DNA ligase can only ligate a 5'-phosphate (Pi) to a 3'-OH, and the cuts generated by restriction enzymes contain 5'-Pi, the linker can only be ligated to the blunt end cuts produced by the restriction enzyme in one orientation, i.e., the 3' of the longer oligomer to the 5' end of the blunt end cut;

5. After ligation, magnetic beads coated with antibodies against digoxigenin are mixed with the DNA sample. Only free linkers and ligated linkers can bind to the antibody on the magnetic beads. The magnetic beads and any cDNA fragments attached to them are then retained by a magnet, while all other non-specific RNA and DNA are washed away. Inactivation of the digoxigenin/antibody interaction releases the fragments of interest from antibodies as an intact double-stranded DNA;

6. The DNA is then mixed with magnetic beads coated with streptavidin, which specifically binds biotin. This allows the DNA fragments that contain a 5'-biotinylated $dT_XM$ to be retained by a magnet while other nonspecific fragments are washed away. The desired fragments of DNA with sequence identical to the original mRNAs of the cell of interest and covalently linked to the longer oligomer of the linker are released from the magnetic beads by alkali denaturation;

7. After these steps of purification, only DNA fragments with the longer oligomer at the 5' end and $dA_X$ at the 3' end remain in solution. These fragments are amplified by PCR using the longer oligomer of the linker labeled with a radioisotope and a specific $dT_XMN$ as primers, where M is dG, dC or dA and N is dG, dC, dA or dT. The final products are separated on a sequencing gel. The series of fragments of different lengths obtained correspond to the various mRNA species fingerprinted by the particular restriction enzyme employed in step 3. The intensity of each fragment reflect the relative frequency of the corresponding mRNA in the starting population.

The individual procedures involved in the newly invented method, i.e., the reverse transcription reaction synthesis of the second strand cDNA, and restriction enzyme digestion are well established, and constant efficiencies are achieved routinely. Magnetic beads coated with streptavidin or with antibody against digoxigenin are commercially available and are widely used. The T4 DNA ligase ligation step and the final PCR step also are widely used and have been shown to be both sensitive and quantitative. Therefore, this new method allows one skilled in the art to detect the exact fingerprint of mRNAs in a specific cell population generated by a particular restriction enzyme. By making use of appropriate restriction enzymes that recognize different DNA sequences, all mRNA species can be fingerprinted quantitatively, even those that exist in low copy number. If closely related cell populations differ in a specific characteristic that results from a difference in gene expression, comparison of fingerprints from such cells can lead to the identification of the gene or genes responsible for that characteristic.

The oligodeoxynucleotide used to prime the reaction of reverse transcriptase is oligo$(dT)_XM$, where M is dG, dC, or dA. The length of the oligo(dT) determines the length of the poly(dA) in the DNA after synthesis of the second strand cDNA, and this poly(dA) serves as the annealing site for the oligo(dT) primer in the PCR amplification step. The use of M at the 3' end of the oligo(dT) primer to anchor the oligo(dT) at the 5' end of the poly A tail of the mRNA ensures the exact length of the poly(dA) stretch at the 3' end of the second strand cDNA. Experience shows that $dT_{24}M$ works efficiently. An equal mixture of $dT_{24}dG$, $dT_{24}dC$ and $dT_{24}dA$ is preferably used, instead of just one of these primers, since reverse transcriptase can sometimes extend a mismatched 3' end. If this were to occur, artifacts would be incorporated into the final result.

The second strand of cDNA can be synthesized in any one of the following ways:

1) An RNAse, such as RNAse H, can be used to generate nicks in the mRNA strand of the mRNA/cDNA hybrid, and then a DNA polymerase, such as the Klenow fragment of *E. coli* DNA polymerase I, can be used to produce the second strand of cDNA by replacement synthesis;

2) Hairpin structures usually form at the 3' end of first strand cDNA. These hairpins can be digested with an endonuclease, such as nuclease S1, and then used to prime the synthesis of the second strand of cDNA by DNA polymerases, such as the Klenow fragment;

3) Arbitrary DNA sequences can be added to the 3' end of the first strand cDNA, either by terminal transferases or RNA ligases, such as T4 RNA ligase, and oligodeoxynucleotides complementary to these arbitrary DNA sequences can be annealed to prime the synthesis of the second strand of cDNA by DNA polymerases, such as the Klenow fragment;

4) Oligodeoxynucleotides, such as random hexamers, can be annealed to the first strand cDNA and extended by a DNA polymerase, such as the Klenow fragment, to produce the second strand of cDNA.

Replacement synthesis has been shown to be particularly efficient for producing the second strand of cDNA.

Most of the restriction enzymes commercially available can be used for this procedure. However, the most useful ones recognize a sequence of six nucleotides and generate a blunt end, so that no fill-in reactions are necessary before ligation of the asymmetric linker. The possibility of a particular nucleotide being recognized and cut by such an enzyme is 1 in 4096 ($4^6$). In theory, if 15,000 mRNA species are transcribed in a particular type of cell, and the most readable regions of a sequencing gel contain fragments of lengths 100 nucleotides (nt) to 300 nt, 732 mRNA species (15000×200/4096) can be fingerprinted by a typical restriction enzyme within that range. Therefore, the use of twenty (20) different restriction enzymes covers essentially all mRNAs expressed in a particular cell. In order to display the 732 individual cDNAs corresponding to these mRNAs within a range of 200 nt, the oligo(dT) primer used in the PCR amplification step should contain two additional nucleotides, M and N, at the 3' end to help differentiate the mRNAs, where M is either dG, dC or dA and N is either dG, dC, dA or dT. Each of the $dT_{24}MN$ primers will cover 1/12 of this fingerprint, i.e., 61 mRNA species, a number which can be well separated and easily distinguished in a 200 nt range.

The purification steps involving anti-digoxigenin-coated beads and streptavidin-coated beads are necessary to free the final fingerprint of interference by nonspecific mRNA species. Because only DNA/DNA duplexes, not RNA/DNA duplexes, can be digested with the restriction enzymes to be used, anti-digoxigenin coated beads will retain only DNA that has been digested and ligated to the asymmetric linker, while all the rest of the DNA and RNA will be washed away. Because streptavidin-coated beads will retain only the DNA with 5' biotinylated oligo(dT), i.e., DNA corresponding to the 3' portion of the original mRNA sequence, after the dual purification process followed by release of the desired strand by alkali denaturation, only the specific fragments generated by the restriction enzyme remain, and these are the fragments that are amplified by the PCR step.

Introduction of ligation mediated polymerase chain reaction into the protocol allows the use of 24-mers or 25-mers to perform the PCR amplification step, instead of the 10 mers that must be used in the DDRT-PCR method of Liang and Pardee (1992). This additional length provides much higher specificity. By using a series of restriction enzymes to fingerprint the mRNA, in theory all mRNA species can be screened. The restriction enzymes to be used typically recognize a sequence of six nucleotides, and any such restriction enzyme can be used without affecting the other steps. A further advantage of the present method is that it is rapid. It requires only two days to prepare the template for PCR amplification after RNA has been extracted. Additionally, since each of the steps involves procedures routinely carried out in molecular biology laboratories, the assay is relatively easy to perform. Finally, since this RERF technique, like DDRT-PCR, is based on PCR, one is able to carry out the analysis with only microgram quantities of RNA. Therefore, the RERF method is very specific and versatile even for use with only limited amounts of RNA.

EXAMPLE 1

Four independent cell populations were chosen to demonstrate the new technique, i.e., SL68, a finite life span diploid human fibroblast cell line; MSU-1.1, an infinite life span, nontumorigenic, near-diploid human fibroblast cell strain; MSU-1.1-6A, a tumorigenic cell line derived from MSU-1.1 after carcinogen treatment, and XP4BE, a finite life span diploid xeroderma pigmentosum variant cell line. The cells were grown to 80% confluency under identical conditions, and total RNA was extracted and purified. Reverse transcription was carried out on cellular RNA (10 μg) at 37° C. in a buffer containing 50 mM Tris.HCl (pH 8.3), 40 mM KCl, 6 mM $MgCl_2$, 10 mM dithiothreitol (DTT), 0.5 mM dNTP, 20 ng/ul of each of the 5'-biotinylated $dT_{24}M$ primers, and 10 units/μl of M-MLV reverse transcriptase (Gibco-BRL, Gaithersburg, Md.). The reaction was stopped after 1 hour. RNaseH (0.3 units) and the Klenow fragment of E. coli DNA polymerase I (4 units) were added along with replacement second strand synthesis buffer so that the final solution contained 10 mM $MgCl_2$, 95 mM Tris.HCl (pH 8.3), 11.5 mM $(NH_4)_2SO_4$, 28.8 mM KCl and 3.8 mM DTT, and the mixture was incubated at 16° C. for 4 hours. After that, 1/20 of the reaction mixture was digested overnight with one of different restriction enzymes, including BsrBI (designated sample 2), PvuII (designated sample 8) and MscI using the buffers supplied by the manufacturer (New England Biolabs (NEB), Beverly, Mass.). The samples were then heated to 65° C. to inactivate the restriction enzymes. An equal volume of 2X ligation buffer (NEB) was added to each sample with 50 pmol of the asymmetric linker (composed of a 5'-digoxigeninated longer oligomer GTCT-TATGTATGTATCTCGAATGCT [SEQ ID NO:1]) and a shorter oligomer AGCATTCGAGAT (SEQ ID NO:2) and 1 unit of T4 DNA ligase (NEB), and the samples were incubated at 16° C. for 16 hours. As described in FIG. 1, the desired fragments were then isolated and purified using anti-digoxigenin-coated magnetic beads (Boehringer Mannheim Biochemicals, Indianapolis, Ind.), followed by streptavidin-coated magnetic beads (Dynal, Oslo, Norway) according to the manufacturers' instructions. The fragments in an aliquot (1/14) of the purified product were then amplified by PCR, using $^{32}P$-end-labeled longer oligomer of the linker and $dT_{24}GG$, in the presence of 35 mM Tris.HCl (pH 8.55), 2.75 mM $MgCl_2$, 60 mM KCl, 16 mM NaCl, 2 μM dNTPs, and 0.1 units/μl of Taq DNA polymerase (Perkin-Elmer, Foster City, Calif.). The PCR parameters were 30 sec at 94° C., 30 sec at 50° C. and 90 sec at 70° C. for 25 cycles followed by incubation at 70° C. for 10 minutes. The fragments were then separated on a sequencing gel.

Figure 2A:
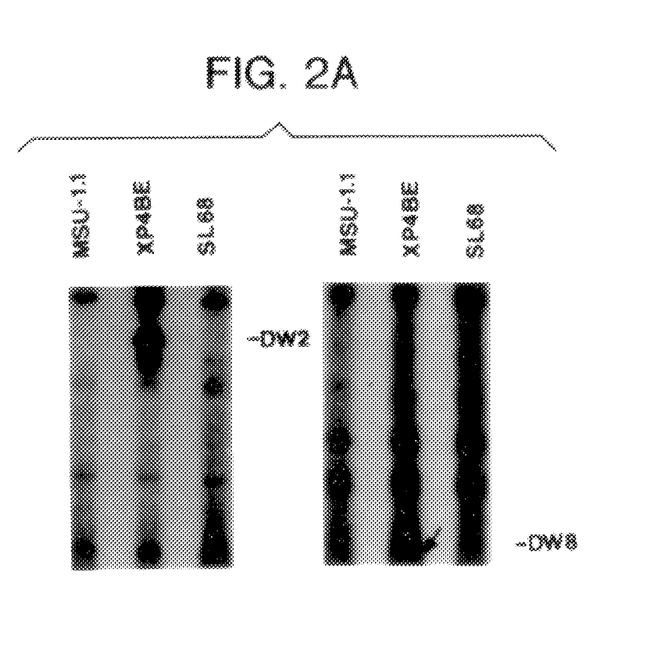
FIG. 2A is a photograph of an autoradiogram showing cDNA fragments of two differentially expressed mRNA species of three independent human fibroblast cell lines, designated MSU-1.1, SL68 and XP4BE, which were detected using the method of the present invention. Two cDNA fragments showing differences were designated DW2 and DW8.
Figure 2B:
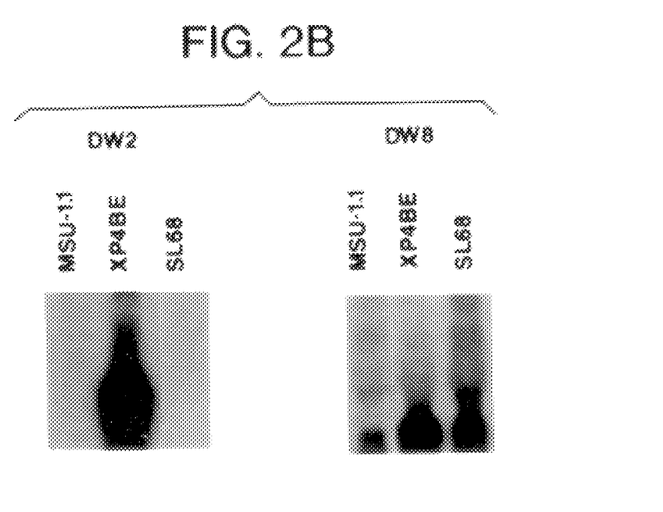
FIG. 2B is a photograph which shows the Northern blotting of cellular RNA from the three corresponding human fibroblast cell lines, using the gel purified DW2 and DW8 fragments as probe.
Figure 3A:
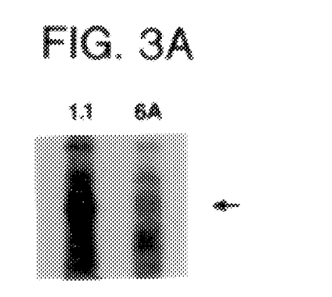
FIG. 3A is a photograph of an autoradiogram showing a cDNA fragment of a differentially expressed mRNA in the RNA fingerprints of MSU-1.1 cells and their tumorigenic derivative, MSU-1.1-6A cells, detected using the method of the present invention. This cDNA fragment, designated DW-A, is indicated by an arrow.
Figure 3B:
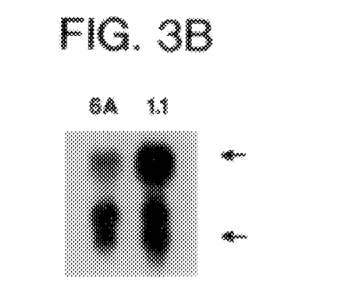
FIG. 3B is a photograph showing Northern blotting of cellular RNA from MSU-1.1 cells and MSU-1.1-6A cells using the gel purified DW-A fragment as probe. Two signals were detected.

After comparing the differentially expressed gene fragments in the four cell lines, three obviously differentially expressed fragments were chosen because of interest in genes expressed in XP variant cell strains but not in normal cells, and in genes expressed in MSU-1.1 cells but not in MSU-1.1-6A cells. Fragment DW2 is expressed in the XP4BE cells, but not expressed in MSU-1.1 or SL68 cells, while fragment DW8 is most abundant in XP4BE cells, and less abundant in SL68 and MSU-1.1 cells (FIG. 2A). DW-A is more abundant in MSU-1.1 cells than in MSU-1.1-6A cells (FIG. 3A). These DNA fragments of interest were cut from the dried sequencing gel and reamplified using the longer oligomer and $dT_{24}GG$. The amplified products appeared as a single band on the agarose gel, and were cut out and purified. The gel-purified DW2, DW8 and DW-A DNA fragments were then labeled with $^{32}P$-dCTP and used to probe a nylon membrane containing cellular RNA from the three cell lines. As shown in FIGS. 2B and 3B, the Northern blotting results confirmed the difference observed in the RNA fingerprint.

Figure 2C:
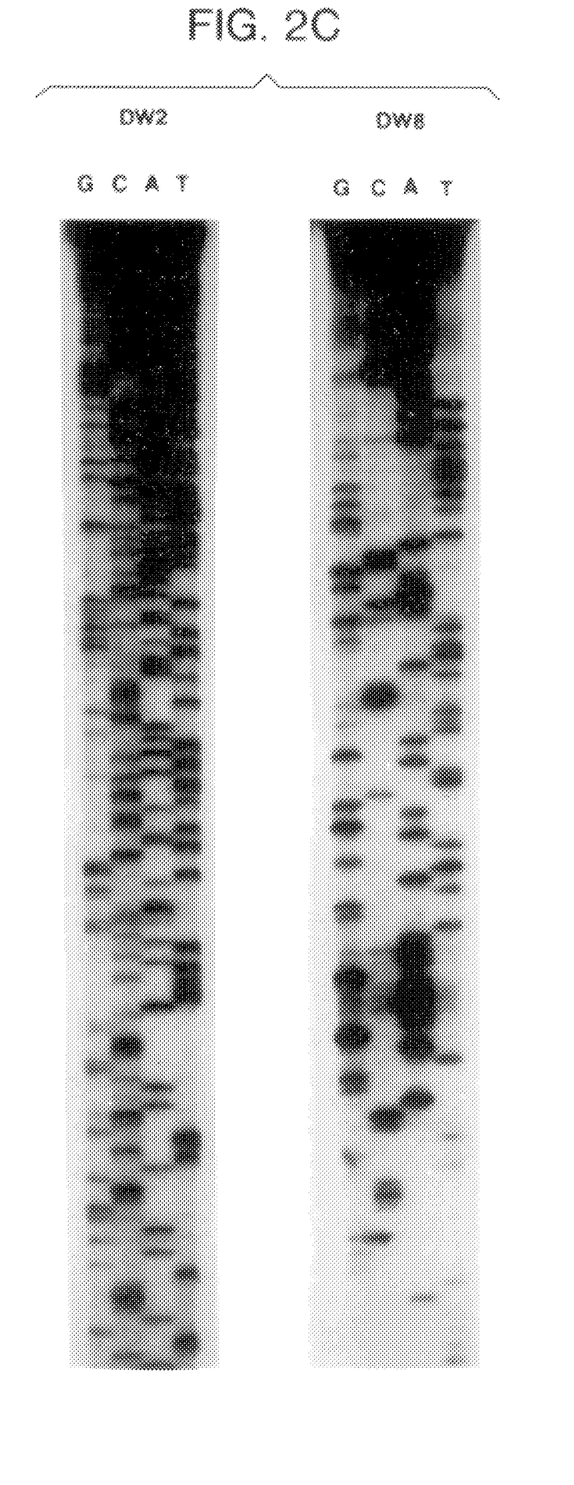
FIG. 2C is a photograph showing the results of directly sequencing the gel-purified fragments of DW2 and DW8 using the method of cycle-sequencing.

The gel-purified DW2 and DW8 fragments were directly sequenced using a TAQUENCE kit (United States Biochemicals, Cleveland, Ohio). As shown in FIG. 2C, the sequence ladders were very clearly separated, indicating that the products were of high purity. GenBank was searched for sequences homologous to those of DW2, DW8 and DW-A. DW8 showed 96% homology to a TGF-β-induced gene product, and DW-A showed 97% homology to the human ferritin gene. However, there was no human gene that DW2 was homologous to. Rather, it showed 89% homology to a putative mycoplasma 16S rRNA gene, suggesting that this cDNA fragment resulted from mycoplasma contamination in XP4BE cells. The presence of a low level of mycoplasma in this batch of XP4BE cells, but not in the SL68 or MSU1.1 cells, was subsequently confirmed using a PCR Mycoplasma Detection Kit (Stratagene, LaJolla, Calif.).

The foregoing description is intended to be only illustrative of the present invention and that the present invention be limited only by the hereinafter appended claims.

We claim:

1. A method for producing DNA from mRNA in a sample, which comprises:

(a) isolating RNA from the sample;
    (b) priming the mRNA with a first synthetic oligodeoxynucleotide that hybridizes with the polyadenylate (polyA) tail of mRNA and one non-adenylate nucleotide, and consists of polydeoxythymidylate (dT) with a 5' and a 3' end, which has a first label at the 5' end and has a deoxynucleotide (M) at the 3' end, wherein M is selected from the group consisting of dG, dC and dA;
    (c) reverse transcribing the mRNA to produce a mRNA:cDNA hybrid;
    (d) producing a double-stranded DNA from the mRNA:cDNA hybrid;
    (e) digesting the double-stranded DNA with a restriction endonuclease to produce a cut in the double-stranded DNA;
    (f) ligating the 5' end of one strand of the double-stranded DNA at the cut to a 3' end of one strand of a complementary pair of second and third synthetic oligodeoxynucleotides that comprise a linker DNA, where one of the strands of the linker DNA is longer than the other, so that the linker DNA has a staggered end and a blunt end, wherein the longer strand of the linker DNA has a second label, different from the first label, at the staggered end, the 5' end, and is the strand of the linker DNA that is ligated at the blunt end to the polyA tail strand of the double-stranded DNA at the cut;
    (g) isolating the double-stranded DNA containing the second label with a first reagent which binds the second label to retain the DNA that has been ligated to the linker DNA;
    (h) isolating the double-stranded DNA containing the first label and second label with a second reagent which binds the first label, wherein the isolated DNA is now free of double stranded DNA containing only the second label;
    (i) amplifying the isolated DNA strand in step (h) which contains the polyA tail by a polymerase chain reaction (PCR); and
    (j) separating the amplified DNA.

2. A method for identifying mRNA produced by a cell population which comprises:

(a) isolating RNA from a population of cells;
    (b) priming the mRNA with a synthetic oligodeoxynucleotide that hybridizes to the polyA tail of the mRNA and has the formula $(dT)_xM$ which has a first label at its 5' end, wherein dT is deoxythymidylate, M is selected from the group consisting of dG, dC and dA and x is a whole number between 20 and 28;
    (c) reverse transcribing the mRNA to produce a mRNA:cDNA hybrid;
    (d) producing a double-stranded DNA from the mRNA:cDNA hybrid;
    (e) digesting the double-stranded DNA with a restriction endonuclease to produce a cut in the double-stranded DNA;
    (f) ligating the 5' end of one strand of the double-stranded DNA at the cut to a 3' end of one strand of a complementary pair of second and third synthetic oligodeoxynucleotides that comprise a linker DNA, where one of the strands of the linker DNA is longer than the other, so that the linker DNA has a staggered end and a blunt end, wherein the longer strand of the linker DNA has a second label, different from the first label, at its staggered end, the 5' end, and is the strand of the linker DNA that is ligated at the blunt end to the polyA tail strand of the double-stranded DNA at the cut;
    (g) isolating the double-stranded DNA containing the second label with a first reagent which binds the second label to retain the DNA that has been linked to the linker DNA;
    (h) isolating the double-stranded DNA containing the first label and second label with a second reagent which binds the first label on double stranded DNA, wherein the isolated DNA is now free of double stranded DNA containing only the second label;

(i) amplifying the isolated DNA strand in step (h) which contain the polyA tail by a polymerase chain reaction (PCR); and (j) separating the amplified DNA, wherein the DNA identifies the mRNA produced by the population of cells.

3. A method for identifying mRNA produced by a set of cell populations which comprises:

(a) isolating RNA from one of the cell populations;

(b) priming the mRNA with a synthetic oligodeoxynucleotide that hybridizes to the polyA tail of the mRNA and has the formula $(dT)_xM$ which has a first label at its 5' end, wherein dT is deoxythymidylate, M is selected from the group consisting of dG, dC and dA and x is a whole number between 20 and 28;

(c) reverse transcribing the mRNA to produce a mRNA:cDNA hybrid;

(d) producing a double-stranded DNA from the mRNA:cDNA hybrid;

(e) digesting the double-stranded DNA with a restriction endonuclease to produce a cut in the double-stranded DNA;

(f) ligating the 5' end of one strand of the double-stranded DNA at the cut to a 3' end of one strand of a complementary pair of second and third synthetic oligodeoxynucleotides that comprise a linker DNA, where one of the strands of the linker DNA is longer than the other, so that the linker DNA has a staggered end and a blunt end, wherein the longer strand of the linker DNA has a second label, different from the first label, at the staggered end, the 5' end, and is the strand of the linker DNA that is ligated at the blunt end to the polyA tail strand of the double-stranded DNA at the cut;

(g) isolating the double-stranded DNA containing the second label with a first reagent which binds the second label to retain the DNA that has been ligated to the linker DNA;

(h) isolating the double-stranded DNA containing the first label and second label with a second reagent which binds the first label, wherein the isolated DNA is now free of double stranded DNA containing only the second label;

(i) amplifying the isolated DNA strand in step (h) which contains the polyA tail by a polymerase chain reaction (PCR);

(j) separating the amplified DNA, wherein the DNA identifies the mRNA produced by the cell population; and (k) repeating steps (a) to (j) with different endonucleases to detect differences in the mRNA in the set of cell populations.

4. The method of claims 1, 2 or 3 wherein in step (i) the isolated DNA is amplified using the poly thymidine MN as one primer of the DNA, wherein M is dG, dC, or dA, and N is dG, dC, dA or dT and wherein the second primer is the longer oligodeoxynucleotide of the linker without the second label.

5. The method of any one of claims 2 or 3 wherein the first label is biotin.

6. The method of any one of claims 2 or 3 wherein the second label is digoxigenin.

7. The method of any one of claims 2 or 3 wherein the first label is biotin and wherein the second label is digoxigenin.

8. The method of any one of claims 2 or 3 wherein in step (b), $(dT)_x$ is $(dT)_{20-28}$.

9. The method of any one of claims 2 or 3 wherein in step (f) the longer oligodeoxynucleotide which contains the second label is as set forth in SEQ ID NO:1 and the other oligodeoxynucleotide is as set forth in SEQ ID NO:2 which form the linker DNA.

10. The method of any one of claims 2 or 3 wherein in step (j) the double-stranded DNA is separated by gel electrophoresis.

11. The method of claim 2 wherein after step (j) the separated DNA is compared for the more than one cell population to determine differences in the mRNA.

12. The method of any one of claims 1, 2 or 3 wherein each of the first and second reagents which bind to each of the first and second labels is attached to a magnetic particle and wherein a magnet is used to separately isolate each of the labeled DNAs.

13. The method of any one of claims 1, 2 or 3 wherein each of the first and second reagents which bind to each of the first and second labels is attached to a magnetic particle and wherein a magnet is used to isolate each of the labeled DNAs, and wherein the second reagent is streptavidin and the first label is biotin and the second label is digoxigenin and the first reagent is an antibody.

14. The method of claim 3 wherein in step (e) at least twenty (20) restriction endonucleases are separately used to digest the double-stranded DNA so as to establish a pattern for comparison between the mRNA from the various sets of cell populations.

15. A kit for producing DNA produced from mRNA in a sample which comprises:

(A) a synthetic oligodeoxynucleotide which has a first label and which is poly(dT)M, wherein M is selected from the group consisting of dG, dC and dA;

(B) a complementary pair of strands of synthetic oligodeoxynucleotides of unequal lengths, that comprise a linker DNA, wherein a longer of the strands has a label at its staggered end which is different from the first label;

(C) a first reagent which binds the second label;

(D) a second reagent which binds the first label; and (E) a set of restriction enzymes.

16. A kit for identifying mRNA in a cell population which comprises in separate containers:

(A) a synthetic oligomer which contains a first label of the formula $(dT)_xM$, wherein dT is polydeoxythymidylate, M is dG, dC, or dA and X is a whole number between 20 and 28;

(B) a complementary pair of synthetic oligodeoxynucleotide strands, one strand of which is longer than the other, that comprise a linker DNA which has a staggered end and a blunt end, wherein the longer one of the strands of the linker DNA has a label at the staggered end which is different from the first label;

(C) a first reagent which binds to the second label; and (D) a second reagent which binds to the first label;

(E) multiple restriction endonucleases.

17. The kit of claim 16 further comprising a first primer which is $(dT)_xMN$, wherein $(dT)_xM$ is defined according to claim 16 and N is dG, dC, dA, or dT and wherein a second primer is the longer oligodeoxynucleotide of the linker without the label.

18. The kit of any one of claims 15 or 16 wherein the first label is biotin.

19. The kit of any one of claims 15 or 16 wherein the second label is digoxigenin.

20. The kit of any one of claims 15 or 16 wherein the first label is biotin and wherein the second label is digoxigenin.

21. The kit of claim 16 further comprising a synthetic oligodeoxynucleotide comprising $(dT)_x$ wherein $(dT)_x$ is $(dT)_{24}$.

22. The kit of any one of claims 15 or 16 wherein the longer oligodeoxynucleotide which contains the label is as set forth in SEQ ID NO:1 and the shorter oligodeoxynucleotide is as set forth in SEQ ID NO:2 which together form the linker DNA.

23. The kit of any one of claims 15 or 16 further comprising a gel electrophoresis separating medium.

24. The kit of any one of claims 15 or 16 wherein the first and second reagents which bind to each of the first and second labels are attached to a magnetic particle and wherein a magnet can be used to separately isolate each of the labeled DNAs.

25. The kit of any one of claims 15 or 16 wherein the second reagent is streptavidin and the first label is biotin and the second label is digoxigenin and the first reagent is an antibody.

26. The kit of claims 15 or 16 which contains a RNA as a control for separate testing.

27. A method for producing DNA from mRNA in a sample, which comprises:

(a) isolating RNA from the sample;

(b) priming the mRNA with a first synthetic oligodeoxynucleotide that hybridizes with the polyadenylate (polyA) tail of mRNA and one non-polyadenylate nucleotide and consists of polydeoxythymidylate (polydT) with a 5' and a 3' end, which has a first label at the 5' end and has a deoxynucleotide (M) at the 3' end, wherein M is selected from the group consisting of dG, dC and dA;

(c) reverse transcribing the mRNA to produce an mRNA:cDNA hybrid;

(d) producing a double-stranded DNA from the mRNA:cDNA hybrid;

(e) digesting the double-stranded DNA with a restriction endonuclease to produce a cut in the double-stranded cDNA;

(f) ligating the 5' end of one strand of the double-stranded DNA at the cut to a 3' end of one strand of a complementary pair of second and third synthetic oligodeoxynucleotides that comprise a linker DNA, where one of the strands of the linker DNA is longer than the other, so that the linker DNA has a staggered end and a blunt end, wherein the longer strand of the linker DNA has a second label, different from the first label, at the staggered end, the 5' end, and is the strand of the linker DNA that is ligated at the blunt end to the strand of the double-stranded DNA at the cut;

(g) isolating the cDNA strand containing the second label free of the cDNA strand containing the first label, comprising the steps of:

(1) isolating the double-stranded DNA with a first reagent which binds the second label to remove the double-stranded cDNA that has not been cut by the restriction enzyme and therefore has not been ligated to the linker DNA (2) isolating the double-stranded DNA containing the polyA tail with a second reagent which binds the first label to eliminate double-stranded cDNA that contains only the second label, then (3) isolating the DNA strand containing the second label free of the cDNA strand containing the first label;

(h) amplifying the isolated DNA strand containing the polyA tail by a polymerase chain reaction (PCR); and (i) separating the amplified DNA.

\* \* \* \* \*